United States Patent [19]
Oratz

[11] Patent Number: 5,813,557
[45] Date of Patent: *Sep. 29, 1998

[54] MAGNETIZED FLUID VESSEL

[76] Inventor: Ben Oratz, 79 Albertson Ave., Albertson, N.Y. 11507

[*] Notice: This patent issued on a continued prosecution application filed under 37 CFR 1.53(d), and is subject to the twenty year patent term provisions of 35 U.S.C. 154(a)(2).

The term of this patent shall not extend beyond the expiration date of Pat. No. 5,542,562.

[21] Appl. No.: 857,771

[22] Filed: May 16, 1997

Related U.S. Application Data

[60] Continuation of Ser. No. 621,467, Mar. 25, 1996, abandoned, which is a division of Ser. No. 364,806, Dec. 27, 1994, Pat. No. 5,542,562.

[51] Int. Cl.$^6$ ................................................ B65D 81/24
[52] U.S. Cl. ..................... 220/23.9; 220/23.86; 206/438; 206/818
[58] Field of Search .................................. 215/386, 387; 206/818, 438; 220/703, 646, 648, 890, 483, 410, 408, 23.83, 23.86, 4.01, 751, 683, 694, 735, 758; 40/310; 248/206.5, 230.8

[56] References Cited

U.S. PATENT DOCUMENTS

| | | | |
|---|---|---|---|
| 337,713 | 3/1886 | Snypp | 215/386 |
| 566,761 | 9/1896 | Hosmer | 40/310 |
| 999,672 | 8/1911 | Puffer | 220/408 |
| 1,725,726 | 8/1929 | Ament | 220/735 |
| 2,314,942 | 3/1943 | Hinchcliff | 220/735 |
| 3,241,699 | 3/1966 | Burg | 215/386 |
| 3,957,171 | 5/1976 | Besser | 220/648 |
| 4,629,087 | 12/1986 | Lenz | 220/694 |
| 5,542,562 | 8/1996 | Oratz | 220/410 |
| 5,547,102 | 8/1996 | Rule et al. | 220/648 |

FOREIGN PATENT DOCUMENTS 2112645  7/1983  United Kingdom.

OTHER PUBLICATIONS

Philpott et al., Biomagnetic Handbook, 1990, pp. 4–12, 16–17, 23–26 and 30.

*Primary Examiner*—Stephen J. Castellano
*Attorney, Agent, or Firm*—Robert L. Epstein; Harold James; James & Franklin, LLP

[57] ABSTRACT

The vessel includes a fluid container or conduit. First and second magnets are situated on opposite sides of the vessel wall and are encircled by a metallic band or collar. The vessel may have an open mouth defined by a rim. In one embodiment, magnets are suspended by hangers form a rim of a cup. The cup and magnets are received in an exterior container with a removable lid. Other embodiments include oxygen tanks, oxygen tubes and containers for intravenous liquids.

7 Claims, 3 Drawing Sheets

FIG.3
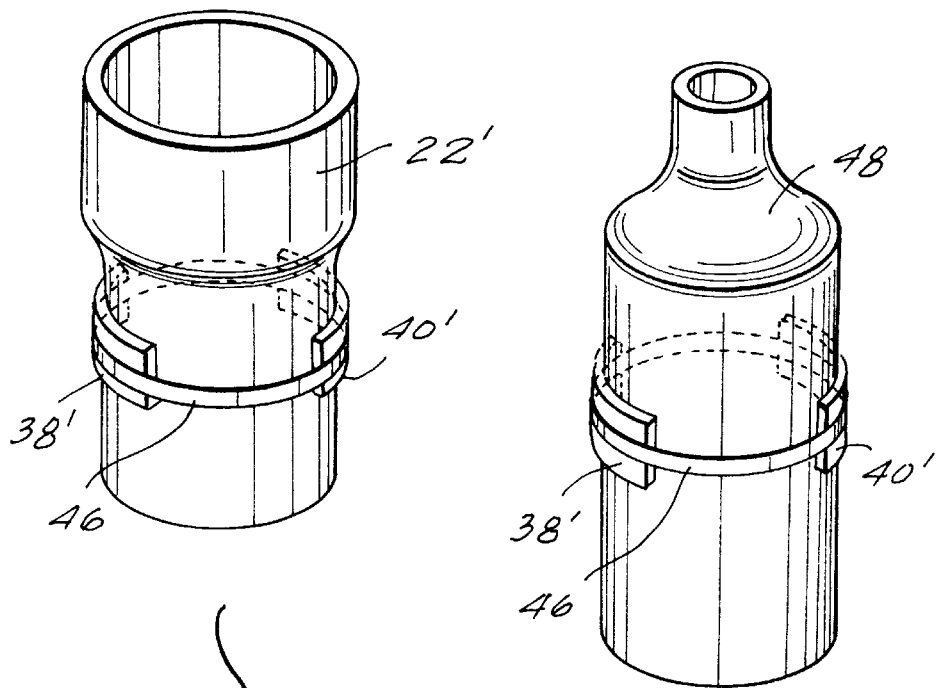
FIG.4
FIG.5
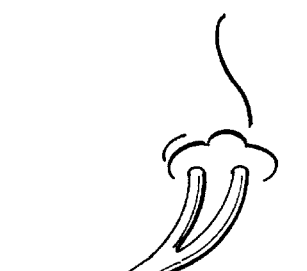
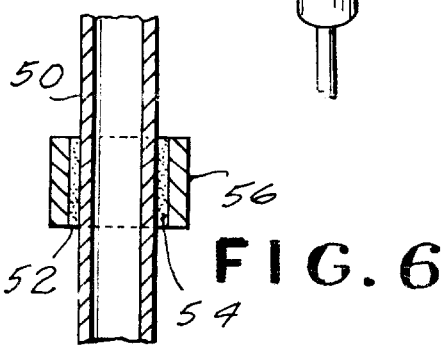
FIG.6
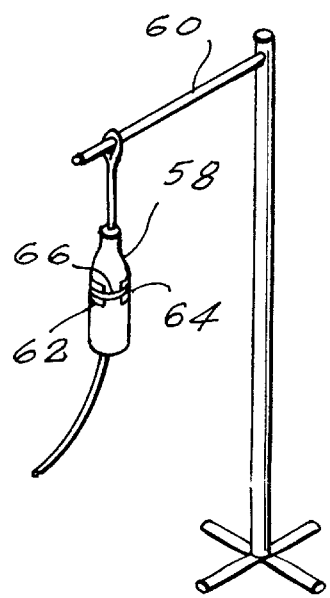
FIG.7

MAGNETIZED FLUID VESSEL

This is a continuation of Ser. No. 08/621,467 of Mar. 25, 1996, now abandoned, which is a Divisional of Ser. No. 08/364,806 of Dec. 27, 1994, now U.S. Pat. No. 5,542,562 issued Aug. 6, 1996.

SUMMARY OF THE INVENTION

The present invention relates to a vessel such as a container or conduit for fluid such as water, oxygen or liquid to be administered intravenously and more particularly to such a vessel which includes magnets mounted on the exterior of the vessel for creating a magnetic field in the fluid.

Certain advantageous biological effects are claimed to occur in people who consume fluids which have been treated by exposure to magnetic fields for short time durations. For example, William H. Philpott, M.D. and Sharon Toplin in their book *Biomagnetic Handbook—A Guide to Medical Magnetics The Energy Medicine of Tomorrow* discuss the theraputic effects of magnetic fields on the body and specifically refer to the beneficial effects of drinking water which has been magnetically treated by placing a glass container of water on or near a magnet for a minimum of five minutes. In other published articles, Dr. Philpott discusses the role of magnetically treated oxygen in health maintenance.

Other means of magnetically treating water are disclosed in U.S. Pat. No. 5,113,751 to Holcomb et al. and in the various magnetic water treatment device patents discussed therein. I am also aware that the chinese have recently claimed theraputic benefits in treating water magnetically. I believe that a H-type magnetized drinking water cup is sold in China.

There is much discussion in Dr. Philpott's work as to the different clinical effects observed by treatment with negative or positive magnetic resonance energy. The poles of a magnet can be identified by a compass, a magnetometer on a gauss meter. For purposes herein, we will define the negative magnetic pole as the same magnetic energy as the negative pole of a direct current and also the same magnetic energy as the earth's north magnetic pole. The positive magnetic pole is identified as the same magnetic energy as the positive pole of a direct current and also the same magnetic energy as the earth's south magnetic pole.

It seems that treating fluids with magnetic fields of different polarity may have opposite effects on the body. Holcomb teaches using magnets of opposite polarity facing each other. The same is true, I believe, of the Chinese drinking cup noted above. However, my research indicates that the best results are obtained using magnets with the negative poles facing each other. Still, I believe that more research must be done in this area and I cannot conclude at this point that magnetic fields other than those created by negative poles facing each other do not have benefit as well.

It is, therefore, a prime object of the present invention to provide a vessel, such as a container or conduit in which a fluid is exposed to a magnetic field.

It is another object of the present invention to provide such a vessel for a fluid such as water, oxygen or a liquid to be intravenously injected into the body.

It is another object of the present invention to provide a magnetized fluid vessel where the magnets are surrounded by a metallic band or collar to enhance the magnetic effect.

In accordance with one aspect of the present invention, a fluid containing vessel is provided comprising a wall with an exterior surface and first and second magnetic means. Means are provided for mounting the magnetic means to the exterior surface of the vessel wall in a position such that the fluid is situated therebetween. The mounting means includes a metallic retaining band.

The vessel may be a tank or a conduit. The fluid may be oxygen. The vessel may be a container for an intravenous liquid.

In accordance with another aspect of the invention, a fluid containing vessel is provided in the form of a container with a wall. First and second magnetic means are provided, each having a portion with a negative magnetic polarity. Means are provided for mounting the magnetic means proximate the exterior container wall with the negative polarity portions facing each other and the fluid situated therebetween. An enclosure is adapted to receive the container and the magnetic means mounted thereon.

The container may be a cup with an open top defined by a rim. The mounting means includes first and second hanger means for hanging the first and second magnetic means on the cup rim. A metal collar encircles the magnetic means. The enclosure comprises a removable lid.

To these and to such other objects as may hereinafter appear, the present invention relates to a magnetized fluid vessel as disclosed in detail in the following specification and recited in the annexed claims, taken together with the accompanying drawings, wherein like numerals refer to like parts and in which:

FIG. 3 is an alternate form of the vessel of the embodiment of FIG. 1;

FIG. 4 is a second preferred embodiment of the present invention;

FIG. 5 is a plan view of a third preferred embodiment of the present invention;

FIG. 6 is a cross sectional view of the third preferred embodiment of the present invention; and FIG. 7 is a fourth preferred embodiment of the present invention.

Figure 1:
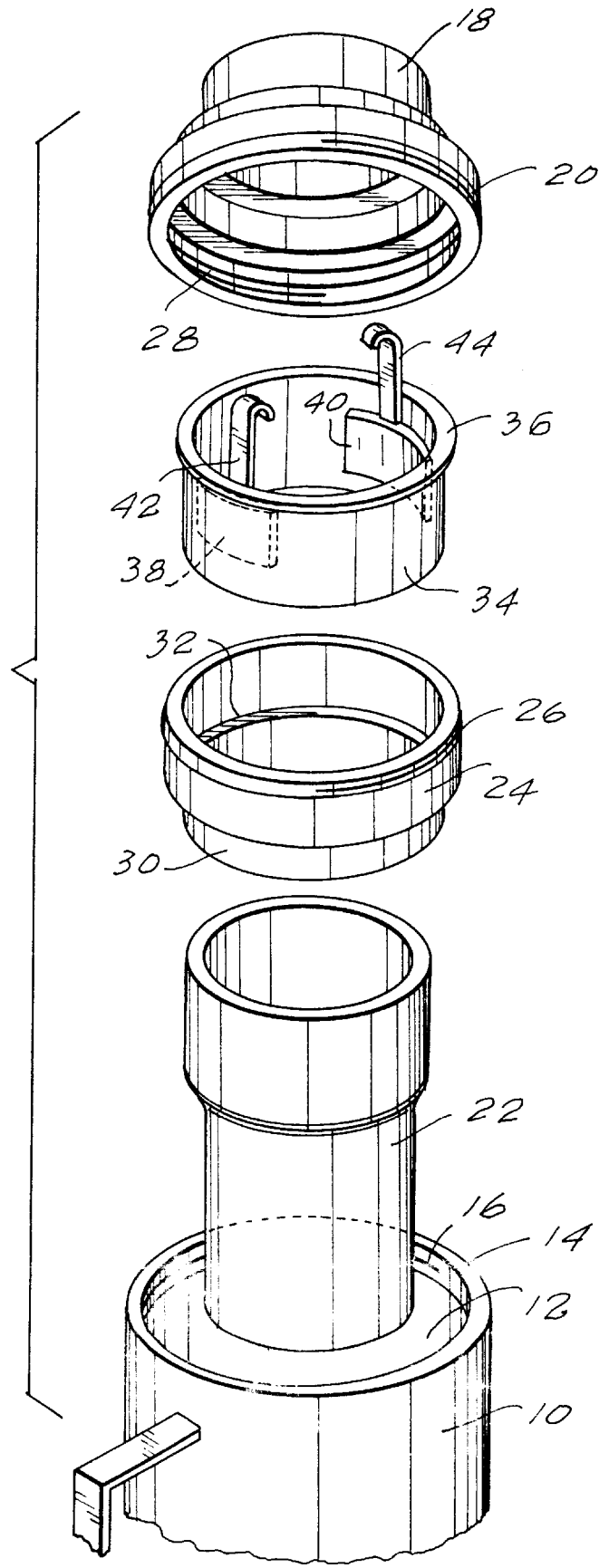
FIG. 1 is an exploded isometric view of a first preferred embodiment of the present invention.
Figure 2:
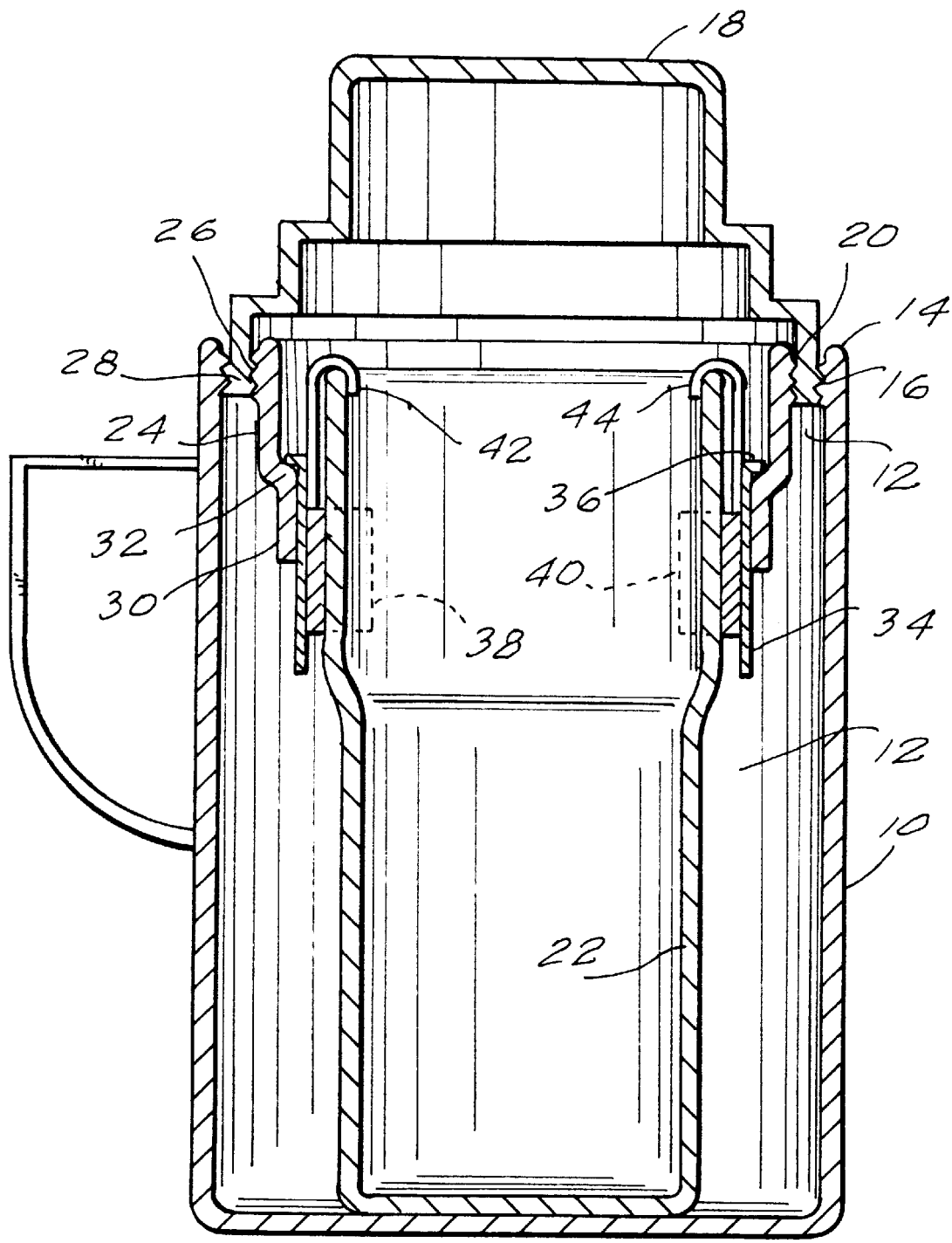
FIG. 2 is a cross sectional view of the embodiment of FIG. 1.

As shown in FIGS. 1 and 2, the first preferred embodiment of the present invention takes the form of an enclosed container for water or other liquid which includes an enclosure 10 composed on non-metallic material such as plastic with a hollow interior, a closed bottom and a wide open mouth 12 defined by a rim 14 which is provided with internal screw threads 16. A lid 18, also made of non-metallic material such as plastic, is provided with external threads 20 so as to engage threads 16 of enclosure 10.

Within the interior 12 of enclosure 10 is situated a open mouth cup 22 also composed of non-metallic material such as plastic. As shown in FIG. 2, container 22 rests on the interior surface of enclosure 10.

A non-metallic collar 24, made of plastic or the like, is provided with an exterior threaded surface 26. Threaded surface 26 is adapted to engage the internally threaded surface 28 of lid 18.

Collar 24 has a bottom portion 30 of smaller inner diameter which forms a shoulder 32. A metallic collar 34 is provided with a flange 36 extending outwardly form the top surface. Collar 34 is received within collar 24 with flange 36 resting on shoulder 32.

Within collar 34 are provided first and second arcuate permanent magnets 38, 40 each of which is attached to a hanger 42, 44, respectively. Magnets 38 and 40 are situated opposite to each other. Preferably each magnet has its negative pole portion facing the interior of the vessel. Hangers 42 and 44 are adapted to hang magnets 38, 40 from the rim of cup 22, as shown in FIG. 2, when the vessel is assembled.

Collar 34 is composed of a magnetic material such as iron or other ferrous metal. It functions to enhance and direct the magnetic field of magnets 38, 40 toward the interior of cup 22.

FIG. 3 shows an alternate form for the cup and magnetic mounting means of FIGS. 1 and 2. In this form, non-metallic container 22' has arcuate magnets 38', 40' strapped to its exterior surface by a metallic band or strap 46 which may be, for example, a stainless still cable tie or similar banding apparatus of the type available from many sources such as Panduit or Band-It-Idex.

As shown in FIG. 4, a similar magnet and mounting structure could be employed with an oxygen supply tank 48. In this case, magnets 38', 40' and strap 46 are situated adjacent the exterior surface of the tank wall.

FIG. 5 and 6 show an alternative structure which can be employed with a plastic oxygen tube or conduit 50 such as the type used to supply oxygen to a patient under medical care. In this case, relatively small arcuate magnets 52 and 54 are employed. Magnets 52, 54 are retained on the exterior wall of tube 50 by a metallic collar 56.

FIG. 7 shows that the magnets and magnetic mounting means can be used in conjunction with a vessel 58 containing a liquid for intaveneous feeding to a patient under medical care. The vessel 58 in the form of a non-metallic bottle or pouch of glass or plastic is hung from a hanger 60. The magnets 62, 64 are retained on vessel 58 by a metallic retaining strap or band 66.

With regard to the embodiment of FIGS. 4–7, it is believed preferrable that the magnets have their negative pole sides facing each other, with the fluid therebetween, for best results. However, beneficial results may also be achieved, but perhaps to a lesser extent, if opposite pole portions face each other.

It should now be appreciated that the present invention relates to a fluid containing vessel, in the form of a non-metallic container or conduit, which has situated proximate thereto a pair of arcuate permanent magnetic adjacent to a field concentrating metallic collar or strap. In one preferred embodiment, the vessel takes the form of an enclosed container cup with a removable lid. In another embodiment, the vessel is an oxygen supply tank or an intravenous liquid supply container. In addition, the magnets can be externally affixed to an oxygen supply tube or conduit.

While only a limited number of preferred embodiments of the present invention are disclosed for purposes of illustration, it is obvious that many modifications and variations could be made thereto. It is intended to cover all of these modifications and variations which fall within the scope of the present invention, as set forth in the following claims:

I claim:

1. A fluid containing vessel comprising a non-metallic cup with an exterior wall, magnetic means having a portion with a negative magnetic polarity and means for mounting said magnetic means proximate said exterior cup wall with said negative polarity portion facing the cup and the fluid situated proximate said magnetic means, a metallic collar encircling said magnetic means and an enclosure adapted to receive said cup and said magnetic means.

2. The vessel of claim 1 wherein said enclosure comprises a removable lid.

3. The vessel of claim 1 further comprising a non-metallic collar.

4. The vessel of claim 1 wherein said wall comprises a drinking cup.

5. The vessel of claim 1 wherein said vessel comprises a container.

6. A fluid containing vessel comprising a non-metallic cup with an exterior wall, magnetic means having a portion with a negative magnetic polarity and means for mounting said magnetic means proximate said exterior cup wall with said negative polarity portion facing the cup, the fluid being situated proximate said magnetic means, and an enclosure adapted to receive said cup and said magnetic means, said cup having an open top defined by a rim and wherein said mounting means comprises first and second means for hanging said magnetic means on said rim.

7. A fluid containing vessel comprising a non-metallic cup with an exterior wall, magnetic means having a portion with a negative magnetic polarity and means for mounting said magnetic means proximate said exterior cup wall with said negative polarity portion facing the cup wall, the fluid being proximate said magnetic means, an enclosure with a removeable lid adapted to receive said cup and said magnetic means, a metallic collar encircling said magnetic means, and a non-metallic collar, said lid engaging said enclosure and said non-metallic collar, said metallic collar engaging said non-metallic collar.

* * * * *